United States Patent [19]

Schell

[11] 4,255,520
[45] Mar. 10, 1981

[54] PROCESS FOR THE PREPARATION OF A RABIES VACCINE AND VACCINE OBTAINED BY THIS PROCESS

[75] Inventor: Klaus R. Schell, Flamatt, Switzerland

[73] Assignee: Schweizerisches Serum-und Impfinstitut and Institut zur Erforschung der Infektionskrankheiten, Bern, Switzerland

[21] Appl. No.: 136,722

[22] Filed: Apr. 2, 1980

[30] Foreign Application Priority Data

Apr. 10, 1979 [CH] Switzerland ............... 3414/79

[51] Int. Cl.$^3$ ......................................... A61K 39/205
[52] U.S. Cl. ......................................... 435/239; 424/89
[58] Field of Search ................... 424/89; 435/235–239

[56] References Cited

U.S. PATENT DOCUMENTS

| | | | |
|---|---|---|---|
| 2,204,064 | 6/1940 | Beard | 424/89 |
| 2,445,300 | 6/1948 | Chambers | 424/89 |
| 2,506,345 | 5/1950 | Cox et al. | 424/89 |
| 2,768,114 | 10/1956 | Koprowski et al. | 424/89 |
| 2,773,800 | 12/1956 | Powell | 424/89 |
| 3,029,190 | 4/1962 | Hanson et al. | 424/89 |
| 3,143,470 | 8/1964 | Wilner | 424/89 |
| 3,155,589 | 11/1964 | Slater | 424/89 |
| 3,156,620 | 11/1964 | Sharpless | 424/89 |
| 3,255,080 | 6/1966 | Emery | 424/89 |
| 3,397,267 | 8/1968 | Fernandes et al. | 424/89 |
| 3,415,926 | 12/1968 | Hays et al. | 424/89 |
| 3,585,266 | 6/1971 | Emery et al. | 424/89 |
| 3,674,862 | 7/1972 | Lavender | 424/89 |
| 3,859,168 | 1/1975 | Barth et al. | 424/89 |
| 3,973,000 | 8/1976 | Cavender | 424/89 |
| 4,040,904 | 8/1977 | Slater | 424/89 |
| 4,071,618 | 1/1978 | Konobe et al. | 424/89 |
| 4,115,195 | 9/1978 | Barth et al. | 424/89 |

OTHER PUBLICATIONS

Bernkopf, H. et al., PSEBM 45: 332 (1940), Characteristics of Fixed Rabies Virus Cultivated on Developing Chick Embryos.
Schell, K. R., A Highly Purified and Concentrated Duck Embryo Vaccine 80th Ann. mtg., Miami Beach, Fla., U.S.A., May 11–16, 1980, Abstr. Annu. Meet AM-Soc. Microbiol. 80(0), 1980, Abstract 821.
Lavender et al., Appl. Microbiol. 22 (3), 1971, 358–365, Zonal Contrifuged Purified Duck Embryo Cell Culture Rabies Vaccine for Human Vaccination.
Kamada Jap, JVETRES, 19 (1–2), 1971, 37–38, Characterization of Multiplication of Avian Encephalomyelitis Virus in Chick Embryo Brain Cell Cultures.
Kuchler Biochemical Methods in Cell Culture and Virology, 1977, Dowden Hutchinson Rossine, pp. 10, 123–130.
Cox Growth of Viruses and Rickettsiae in the Developing Chick Embryo Ann. N.Y. Acad. Sci., vol. 55, Art 2, 236–247 (1952).
Beveridge et al., The Cultivation of Virus and Rickettsiae in the Chick Embryo Med. Res. Counc. G.B. Spec. Rep. Serv. 256 (1946), 92, pp. USPTO#QR66B4 esp., pp. V–VII, 1–39, 67 (Rabies).
Sigurdsson, B. J., Exp. Med. 78:341 (1943) Yield of Rabies Virus in Chick Embryo.
Kliglerij, et al. Nature 143: 899 (1939), Cultivation of Rabies Virus in Developing Chick Embryo.
Dawson, Jr., Amer. J. Path. 17: 177 (1941), Study of Chick Embryo-Adapted Rabies Virus.
Dawson, Jr. Science 89: 300 (1939), Infection of Chicks and Chick Embryos with Rabies.

*Primary Examiner*—Shep K. Rose
*Attorney, Agent, or Firm*—Toren, McGeady & Stanger

[57] ABSTRACT

A method for preparing a rabies vaccine wherein rabies viruses are multiplied in poultry embryos, the heads of the embryos are harvested and the cell extract containing the rabies antigens is separated therefrom for differential centrifugation and density gradient centrifugation, the separated antigen is further processed using conventional methods. This process results in a highly selective concentration of antigens and the production of viruses having a very high activity and freedom from contaminating proteins.

3 Claims, No Drawings

PROCESS FOR THE PREPARATION OF A RABIES VACCINE AND VACCINE OBTAINED BY THIS PROCESS

BACKGROUND OF THE INVENTION

1. Field of the Invention

The present invention relates to a new process for the preparation of a substantially improved rabies vaccine having a high content of active substance in proportion to contaminating proteins and fats, i.e., a particularly high specific activity, and to the vaccine thus obtained.

2. Description of the Prior Art

Rabies vaccines have hitherto been obtained from the brains of rabbits, rats or mice, in which the viruses have been multiplied in the living animal by direct intracerebral inoculation of rabies viruses of standardized seed strains. Various disadvantages are associated with these processes:

1. The veruses are grown in the living animal, which is exposed to great suffering during the procedure and finally must be sacrificed.
2. The inoculation of the living animal, the keeping of the animals and the harvesting of the viruses from their brains cannot take place under such completely hygienically perfect and sterile conditions as, for example, in the case of multiplication of the viruses in vitro or in the egg.
3. The removal of the brain of rabbits, rats or mice a few days old requires a very difficult and troublesome operation technique. In addition, with the smallness and viscous consistency of these brains, the losses of brain matter are considerable.
4. The viruses grown in living animals are contaminated with proteins which have a relatively high content of myelin, a protein-containing substance, which, when the vaccine is used, gives rise to side-reactions which can increase to encephalitis. The myelin content can be reduced, but not avoided, by using very young animals which are only a few days old for multiplication of the virus.

An improvement has been achieved by multiplying the rabies viruses in duck embryos. On the one hand, the use of living animals is thereby avoided, and on the other hand, the content of myelin in embryonal tissue is relatively low, if this compound is present at al.

Nevertheless, the rabies vaccine obtained from duck embryos still has considerable disadvantages compared with the ideal vaccine. The virus suspension obtained from the embryos contains a high proportion of proteins which, because of the nature of the suspension of cells and viruses, cannot be separated or can only be incompletely separated in an economic manner by known methods. The higher the protein content of vaccines, the higher the occurrence of undesirable side reactions when the vaccine is used. On repeated vaccination, which is essential for certain professional people, such as, hunters, foresters, and veterinary surgeons, these side reactions can increase to violent allergic defense reactions against the foreign protein.

A better vaccine can be achieved by multiplication of rabies viruses in virto in human diploid cell cultures. In this context, see H. Koprowski, Laboratory Techniques in Rabies by M. M. Kaplan and H. Koprowski, WHO Monograph Series No. 23, Chapter 28, pages 256–60 (1973): Vaccine for man prepared in human diploid cells; T. J. Wiktor, Develop. biol. Standard, Volume 37, pages 265–66, S. Karger, Basle 1978: Production and control of rabies vaccines made on diploid cells; and T. J. Wiktor et al, Develop. biol. Standard, Volume 40, pages 3–9 (1978): Development and clinical trial of rabies vaccine of tissue culture.

The vaccine thus obtained contains, as an impurity, human proteins which produce less side reactions than foreign proteins.

A considerable disadvantage of this method is the relatively low rate of multiplication of the rabies viruses on diploid fibroblast cells, which makes 10- to 25-fold concentrations necessary for the preparation of the vaccine. This method is thus not efficient enough to meet the world-wide demand for rabies vaccine within the scope of the economic possibilities.

SUMMARY OF THE INVENTION

I have discovered an economical process for the production of a rabies vaccine which avoids the disadvantages of the known methods and, at the same time, yields a vaccine which has a better ratio of antigen value to protein content and, from a qualitative point of view, comes close to the ideal vaccine.

This new process comprises using known methods for cultivating and harvesting rabies viruses in poultry embryos, but using only the heads of the embryos. The cell extract obtained therefrom is composed of a significantly large proportion of substances which have a lower or greater density than that of the rabies antigen. These are separated off by differential centrifugation and density gradient centrifugation, while at the same time, the rabies antigen is selectively concentrated. The resulting purified antigen concentrate is then further processed to the ready-to-use vaccine by known methods.

The vaccine thus obtained is distinguished by a considerably increased activity in relation to contaminating proteins and thus produces reliable protection against rabies infections without triggering off side effects.

DESCRIPTION OF THE PREFERRED EMBODIMENT

Suitable species of poultry for multiplication of rabies viruses in their embryos include ducks, chickens and quails.

The two steps used in the present invention, i.e., the use of only the heads of the embryos and the density centrifugation and differential gradient centrifugation, serve the same purpose of decreasing the content of undesired foreign substances and of simultaneously selectively concentrating the desired immunogenic active substance. These are suited to one another from an organic point of view. Thus, it is only possible to separate the undesired proteins if the virus content of the cell extracts obtained by comminution is sufficiently high so that these extracts can be diluted and thus made readily capable of flow and pumpable without lowering the virus content to below the required level.

This concentration is achieved only if the heads of the embryos are used since the heads have the highest concentration of viruses and the trunks of the embryos contain only about 10% of the viruses of the total body. The rabies vaccine obtained in accordance with the present invention is thus characterized in that it has been harvested from only the heads of poultry embryos in which the rabies virus has been multiplied. As a result, the virus concentration in relation to the protein content is increased more than 3-fold by harvesting only the heads of the embryos.

Sterile duck embryo head pools are homogenized in a blender with an appropriate amount of phosphate buffer solution to give a 5 to 33% strength suspension. In addition to a phosphate buffer of 0.75% of di-sodium hydrogen phosphate, 0.145% of potassium dihydrogen phosphate, and 0.48% of sodium chloride in distilled water (pH 7.4), it is also possible to use other salt solutions customary in the production of virus vaccines. Desalinated water can also be used as a diluent, providing that the pH is kept in the range from 7 to 8.

The predominant proportion of the residual proteins are separated by differential centrifugation, i.e., pre-purifying centrifugation of the dilute suspension of the very finely comminuted embryo head homogenate at about 10,000 xg to 15,000 xg. Subsequent density gradient centrifugation of the supernatant liquor is carried out in a known manner at 15,000 to 90,000 xg with the aid of sugar solutions of different concentrations and of buffer solutions, i.e., increasing sugar concentrations and in buffer solution. For this centrifugation, the pre-purified suspension is pumped at 15,000 to 90,000 xg and at a flow rate of 4 liters/hour over the initially introduced sugar solutions, the concentrations of which increase in a stepwise gradient (usually from 15 to 55% strength sucrose).

The density, protein and antigen content and sterility of the fractions of the various densities collected are determined. The fractions containing antigens are pooled, tested again and then further processed into the vaccine.

Physiological salt solutions of all types, for example, the above-mentioned phosphate buffer, can be employed for the dilution. In this context, see Entenembryo Tollwutvakzine (Duck Embryo Rabies Vaccine), J. M. Hoskins, Laboratory Techniques in Rabies by M. M. Kaplan et al, WHO Geneva 1973, Chapter 27, pages 243–255; Dichtegradientenzentrifugation (Density Gradient Centrifugation), J. Hilfenhaus et al, Journal of Biological Standardization 1976, 4, 263–271; M. Majer et al, Develop. biol. Standard, Volume 37, pages 267–271 (1977); and P. Atanasiu et al, Develop. biol. Standard, Volume 40, pages 35–44.

About 85% of the residual protein content is eliminated by these selective centrifugation operations. The vaccine obtained according to the invention can thus be improved up to 80-fold compared with customary duck embryo rabies vaccine.

This vast improvement is to be attributed to the approximately 20-fold decrease in the protein content and the simultaneous release of many more viruses per embryo. During the working up, fewer viruses are lost by bonding to the cell surfaces and by volumetric and mechanical losses. The volumetric losses arise when large amounts of cell debris are centrifuged off in the sediment, and the mechanical losses arise on centrifugation of relatively viscous suspensions in which more viruses and virus aggregates are also precipitated.

When young mammals (rabbits, rats and mice) are infected by cerebral inoculation of rabies viruses, it is clear that multiplication of the viruses first takes place in the brain. It is surprising, however, that inoculation into the yolk bag of a poultry egg which has started to hatch, also produces multiplication in the brain to a great extent, i.e., about 90% (see Example 2A). Thus, the virus migrates from the yolk bag into the embryo and preferentially attacks the nerve tissue in the process of formation.

Also, in view of the known possibility of multiplying rabies viruses in cell cultures which bear no relationship to nerve tissue, this phenomenon could not be reliably predicted. In this context, see Canadian Pat. Nos. 827,637 and 811,119, Multiplication of rabies viruses in vitro on hamster kidney cell cultures. T. J. Wiktor, Develop. biol. Standard, Volume 37, pages 265–266 (S. Karger, Basle 1977). T. J. Wiktor et al, Develop. biol. Standard, Volum 40, pages 3–9 (1978); Development and production of rabies vaccine on human diploid cells (lung fibroblasts). P. Atanasiu et al, ibid, 40, pages 35–44 (1978), Human rabies vaccine on bovine fetal kidney cells. A. L. van Wenzel et al, ibid 40, pages 69–75 (1978), Production of rabies vaccine in dog kidney cells. J. F. Lavender et al, Applied Microbiology, September 1971, Volume 22, No. 3, pages 358–365, Duck embryo cell culture for rabies vaccine.

It was also not to be expected, a priori, that embryo tissue only in the process of formation already has such markedly organ-specific cells which are thus selectively susceptible to viruses. In this context, see J. F. Lavender et al, loc. cit.

In any case, it has been conventional to always harvest and use the entire embryo body in the preparation of the virus and cell homogenate for the preparation of rabies vaccine by multiplication of the viruses in duck eggs which have started to hatch. In this context, see J. M. Hoskins, Laboratory Techniques in Rabies by M. N. Kaplan et al, WHO, 1973, Chapter 27, pages 243–55, Duck Embryo Vaccine. The entire embryo is also harvested in the analogous preparation of live rabies vaccine in which the multiplication takes place in poultry eggs. In this context, see H. Koprowski, Laboratory Techniques in Rabies, Chapter 26, pages 235–42, Chicken Embryo Vaccine.

By using the embryo heads alone, after homogenization thereof, a suspension which has a very high virus concentration is obtained. It can be diluted and thus, as described above, converted into a form necessary for separating the proteins by differential centrifugation and density gradient centrifugation. If the whole embryo is used, as always happens in the processes hitherto described, see Hoskins loc. cit., after homogenizing the 33% strength extract and centrifuging off the coarse particles at about 2,600 revolutions per minute, a suspension which is relatively viscous and consequently cannot be used for density centrifugation is formed.

The vaccine concentrate obtained by the process according to the present invention is not only distinguished by its high content of far more than 100 antigen value units (measured on a NIH standard by means of the Standard NIH test in mice and the RFFIT test) per mg of nitrogen, it is obtained using embryos which are unborn and not yet sensitive to pain and in which the brain tissue which is still in the process of development, appears to be free from myelin. In this context, see M. Abdussalem et al, The problem of anti-rabies vaccination, International conference on the application of vaccine against assay viral rickettsial and bacterial diseases of man, Pan Am. Health Org. (PAHO), Sc. pub. No. 226 (1970) pages 54–59; and P. Fenje, The status of existing rabies vaccines, ibid pages 60–65.

Myelin could not be detected in a 50% strength brain homogenate from duck embryos by means of polyacrylamide gel electrophoresis while under identical conditions, myelin could be detected in the brain of adult ducks and cattle.

Virtually unlimited amounts, or at any rate, amply sufficient amounts, of the desired valuable and harmless vaccine can be prepared economically and relatively easily by the present process. This is impossible in the case of the preparation of rabies vaccine by multiplication of the viruses in human diploid cell cultures as a result of the low efficiency of this preparation. In this context, see Direction of the "Centre for Diseases Control" CDC of February 1979. The CDC has reduced the use of human diploid cell rabies vaccine to persons who, as a result of duck embryo vaccine, have suffered reactions which have endangered their lives, or were unable to achieve an adequate titre of antibodies. The insufficient productivity of human diploid cell cultures is given as the reason. See also, Morbidity and Mortality, Weekly Report (MMWR) 27, 333,413 (1978).

Since the preparation of rabies vaccine using mammals which have been born, and are with certainty suffering, can no longer be justified, in view of the desire to avoid animal suffering as well as insufficient tolerance and reliability, there is a great need for a new rabies vaccine which is simple to prepare, inexpensive, effective and reliable, this vaccine being the only effective agent for combating the virtually worldwide fatal infectious disease.

In the following table, characteristic determining data of rabies vaccines which have been prepared by known, customary processes (Vaccines A–F) and the corresponding data for a vaccine prepared according to the present invention (G) are listed.

| | AGV-U/ dose | Prot. content/ dose (mg) | AGV-U/ mg of Prot. | Brain-matter in the starting material of one dose[1] (mg) |
|---|---|---|---|---|
| A:<br>Rabbit brain vaccine<br>5% of brain<br>2 ml dose | | 3.4 | | 100 |
| B:<br>Baby mouse brain vaccine<br>1% of brain<br>2 ml dose | | 0.3 | | 20 |
| C:<br>Rat brain vaccine<br>10% of brain<br>1.5 ml dose | | 4.8 | | 150 |
| D:<br>Sheep brain vaccine<br>5% of brain<br>5 ml dose | | 8.5 | | 250 |
| E:<br>Duck embryo vaccine according to Hoskins 33% strength suspension | 0.6 | 11 | 0.05 | 100 (20)[2] |
| F:<br>Human cell culture vaccine according to Koprowski | 2.5 | 20–50 | 0.05–0.125 | 0 |
| G:<br>Purified duck head embryo vaccine according to the present invention | 2.5 | 0.6–1.2 | 3–5 | 15 |

[1]Estimated values
[2]100 mg: head extract, about one fifth thereof is brain = 20mg
Antigen value units AGV-U: Factor by which a vaccine provides moreor less protection against rabies thana NIH reference vaccine
Prot. = Protein Comments:

The superiority of vaccine G obtained according to the invention compared with the vaccines A–F, can clearly be seen from the comparison figures. For all parameters taken into consideration, this new vaccine achieves or exceeds the quality of the best vaccines known hitherto. The protein content is lower only in the case of the baby mouse brain vaccine. In the case of this vaccine B, however, it must be considered that the myelin content can produce encephalitis. The human cell culture vaccine F, which contains no brain tissue, has a high protein content. The specific gravity, i.e., the ratio between the active substance content and the contaminating proteins, is powers of ten higher in the vaccine according to the invention than in the comparison preparations.

EXAMPLE 1

Preparation of Duck Embryo Vaccine

1. Preparation of the Virus Suspension

The "Wistar Rabies, PM (Pitman-Moore)-HDCS" virus strain from the Wistar Institute, Philadelphia, or another rabies virus stain suitable for the preparation of vaccine is adapted to duck embryo cells, before actual use, by intracerebral passage in mice and repeated passages in duck eggs which have just started to hatch.

The viruses from a passage with a particularly high titre, which have already proved suitable in the preparation of rabies vaccine in accordance with the method of J. M. Hoskins (Laboratory Techniques in Rabies by Kaplan et al, WHO, 1973, 27, pages 243-55, Duck Embryo Vaccine), are used for the vaccine production.

Fertilized duck eggs from healthy flocks are incubated at 36° C.±1° C. and at 65 to 70% humidity. After 6 days, they are irradiated with light and unsuitable eggs are removed.

On the 7th day of incubation, the rabies virus is inoculated directly into the yolk bag of the eggs with developing embryos. Incubation is continued. 10-13 days later, the eggs are again irradiated with light. The eggs in which the embryos have continued to develop well are opened under sterile conditions and the embryos are removed and decapitated. The heads are individually stored under sterile conditions in the vapor phase above liquid nitrogen until the test for their sterility has been concluded. The sterile heads are combined in pools of 40 to 60 heads; the sterility of each pool is again tested. For processing to the vaccine, several pools are thawed at 4° to 37° C. and comminuted in a homogenizer (blender) in phosphate-containing buffer (pH 7.4) such that a 5% strength weight/volume head extract is formed.

In addition to NaCl/phosphate buffer (=0.75% of disodium hydrogen phosphate, 0.145% of potassium dihydrogen phosphate and 0.48% of sodium chloride in distilled water), it is also possible to use for the dilution other harmless salt solutions including desalinated water, which are customary in virus vaccine production as long as the pH is kept in the range from 7 to 8.

2. Inactivation of the Viruses

β-propiolactone (BPL) is usually used for the inactivation. In this context, see G. A. LoGrippo, Annales New York Academy of Sciences, Volume 83 (1960), pages 578–94. However, other agents have also been recommended and tested. In the USA, for example, tri-(n-butyl)phosphate is used. In this context, see H. Tint et al, Symposia series in immunobiological standardisation (Karger, Basle) 21, 132–144, A new tissue culture rabies vaccine, inactivated and disaggregated with tri-(n-butyl)phosphate. T. J. Wiktor et al, Develop. biol. Standard, Volume 40, pages 3–9 (1978).

For inactivation with β-propiolactone, the virus-containing tissue suspension is brought to 37° C., whilst stirring continuously and a freshly-prepared, ice-cooled aqueous solution of β-propiolactone is added in an amount such that a concentration of β-propiolactone of 1:2,500 is achieved. After stirring the suspension at 37° C. for 5 minutes, it is transferred to a second vessel and stirred for a further 120 minutes. The pH and temperature are monitored continuously. A fall in the pH is a measure of the BPL hydrolysis and is also recorded as such. The pH drops from about 8 to about 7.4. The suspension is now cooled to 5° C.±3° C. and stirring is continued overnight. The next day, thiomersal [o-(ethylmercurithio)-benzoic acid] is added until a concentration of this antiseptic agent of 1:10,000 is reached. The suspension is kept at 5° C. until purification and concentration by differential centrifugation and density gradient centrifugation.

3. Differential Centrifugation and Density Gradient Centrifugation

The 5% strength head suspension has, for example, a specific activity of 0.78 AGV-U/mg of protein. In a subsequent production batch, an activity of 0.55 AGV-U/mg of protein was measured. The inactivated viruses contained in this suspension are purified and concentrated by two centrifugation operations.

3.1 The coarser cell debris is first removed by pre-purification centrifugation at 10,000 to 15,000 xg. After the pre-purification, the specific activity increases slightly, in batch 1 to 1.0 and in the 2nd batch to 0.73 AGV-U/mg of protein.

3.2 The pre-purified material is then further purified and concentrated by means of centrifugation over a linear sucrose gradient (15–55%) at 75,000 to 90,000 xg.

The sterility and antigen content of the gradient fractions are tested. In these fractions, the specific activity varies with the various densities of the contaminating proteins. Thus, for example, at a density of 19% of sucrose, a specific activity of 2 is found, at 37% the specific activity is 24 and at 43% it is about 6. In a second batch, the specific activity at 20% of sucrose is 0.3, at 37% is above 20 and at 45% is about 2.

Sterile fractions with an activity of over 20 AGV-U/mg of protein (that is to say more than 100 AGV-U/mg of N) and a sucrose content of about 30 to 40% are combined and their sterility and antigen concentration are then tested again and noted for the further process.

4. Formulation of the Antigen Concentrates

Pre-tested antigen concentrates are combined, and diluted to a concentration of at least 2.5 AGV-U/ml with a suitable stabilizer, for example, sodium phosphate buffer (pH 7.4)—see above—or other physiological salt solutions, including the stabilizer already described (see Hoskins, loc. cit). The sterility and antigen value are tested again.

Typical values for this "final bulk" (batch ready for filling into small bottles) are in the range of 3–5 AGV-U/ml, with a specific activity of 3–6. In 5 typical production batches, the specific activities were 2.9, 3.5, 5.1, 5.3 and 5.4.

5. Lyophilization

The "final bulk" obtained according to 4. is filled into small 3 ml bottles in portions of 1 ml. Lyophilization stoppers are loosely placed in the bottles and the vaccine is dried in the frozen state in vacuo. When drying has ended, the stoppers are pressed in and the small bottles are sealed definitively with metal caps to hold the rubber stoppers firmly and are stored at −20° C.

6. Reconstitution to the Ready-to-Use Vaccine and Use of this Vaccine

For use, 1 ml of sterile, distilled water is injected in through the rubber stopper and the small bottle is shaken slightly, without producing foam, until the vaccine has dissolved completely. The entire contents of a small bottle is then injected subcutaneously into the upper arm.

7. Quality Control of the End Product

This comprises: determination of the antigenicity, sterility, inactivity and harmlessness and of the content of nitrogen, NaCl, β-propiolactone residues and thiomersal.

Antigenicity: Test in accordance with the standard instructions of the National Institute of Health (U.S.A.).

Sterility: All the resulting end products which are used are sterile.

Inactivity: This is determined in each case on 3 young rabbits and 10 mice which were observed for 14 days after intracerebral inoculation of 0.3 ml of rehydrated vaccine. The animals should display no symptoms of disease.

Harmlessness: 5 ml of reconstituted vaccine solution are administered intraperitoneally to 3 guineapigs and 0.5 ml is administered intraperitoneally to 3 mice. The animals should exhibit no reactions deviating from the norm.

Stability of the vaccine, obtained according to the example, in lyophilized form:

Activities (AGV-U/ml) in percent of the starting value (0 value) after 3 months at the temperature indicated.

| Lot No. | 0 Valve (AGV-U/ml) | −20° C. | +4° C. | Room temp-erature | +37° C. |
|---|---|---|---|---|---|
| 78 LyII T3 | 3.3 | 124% | 97% | 94% | 70% |
| 78 LyII T4 | 3.7 | 103% | 76% | 100% | 86% |
| 78 LyII T5 | 3.6 | 122% | 75% | 69% | 114% |

Stability of the new rabies vaccine, obtained according to the present invention, after reconstitution:

Activities (AGV-U/ml) in percent of the starting value after 4 weeks storage at the temperature indicated.

| Lot No. | 0 Value (AGV-U/ml) | +4° C. | Room temperature | +37° C. |
|---|---|---|---|---|
| 78 LyII T3 | 3.3 | 136% | 82% | 61% |
| 78 LyII T4 | 3.7 | 135% | 86% | 51% |
| 78 LyII T5 | 3.6 | 125% | 89% | 61% |

EXAMPLE 2

1. Distribution of the Rabies Antigen in the Duck Embryo

In order to determine the distribution of the rabies antigen in the duck embryo, infected duck embryos were divided into head, spinal cord and trunk without central nervous system. The virus content and antigen content were measured:

|  | Heads | Spinal Cord | Trunk without central nervous system |
|---|---|---|---|
| Average values (g) | 3.44 | 0.95 | 9.68 |
| Virus content of the 33% strength suspension (titre × log$_{10}$) | 5.95 | 4.7 | 4.55 |
| Total virus content (log$_{10}$) | 8.50 | 6.7 | 7.55 |
| AGV-U/ml of the 33% strength suspension | 1.9 | <0.3 | <0.3 |

Almost 10 times more virus was found in the head, which makes up about ¼ of the total body, than in the rest of the duck embryo body. It follows, that 75% of the unnecessary and harmful duck embryo protein can be removed by removing the trunk, without noticeably reducing the virus content.

2. Determination of the Optimum Harvesting Time

In a three-part experiment, embryos of different ages were inoculated and were harvested at different times after the inoculation. The heads and trunks were processed separately. The virus content of the heads was determined.

(a) Nine-day old duck embryos were inoculated by the standard procedure (Hoskins, loc. cit.) and were harvested 11, 12, 13, 14 and 15 days later.

|  | Harvesting day (days after inoculation) | | | | |  |
|---|---|---|---|---|---|---|
|  | 11 | 12 | 13 | 14 | 15 |  |
| Harvested weight (g per 20 embryos) | 76 | 88 | 100 | 131 | 135 | heads |
|  | 145 | 179 | 221 | 278 | 290 | bodies |
|  | 221 | 267 | 321 | 409 | 425 | total embryo |
|  | 34 | 33 | 31 | 32 | 32 | proportion of head in % |
|  | 5.8 | 5.7 | 5.3 | 5.1 | 5.2 | virus titre (× log$_{10}$) |

(b) Same as (a) but eight-day old duck embryos were used.

|  | Harvesting day (days after inoculation) | | | | |  |
|---|---|---|---|---|---|---|
|  | 11 | 12 | 13 | 14 | 15 |  |
| Weight of in each case 20 embryos | 60 | 67 | 89 | 113 | 115 | heads |
|  | 102 | 137 | 195 | 247 | 260 | bodies |
|  | 162 | 204 | 284 | 359 | 375 | total embryo |
|  | 36 | 33 | 37 | 29 | 30 | proportion of head in % |
|  | 5.9 |  | 5.7 |  | 5.1 | virus titre (× log$_{10}$) |

(c) Same as (a) but seven-day old duck embryos were used

|  | Harvesting day (days after inoculation) | | | | |  |
|---|---|---|---|---|---|---|
|  | 11 | 12 | 13 | 14 | 15 |  |
| Weight of in each case 20 embryos | 62 | 65 | 83 | 91 | 99 | heads |
|  | 108 | 130 | 176 | 226 | 235 | bodies |
|  | 170 | 195 | 259 | 317 | 334 | total embryo |
|  | 36 | 33 | 37 | 29 | 30 | proportion of head in % |
|  | 5.6 | 5.8 | 5.5 | 5.2 | 4.9 | virus titre (× log$_{10}$) |

From these data, it can be seen that (1) the head is about ⅓ of the total embryo and (2) the highest virus titre is already achieved on the 11th day after the inoculation. Since the rabies antigen is primarily of interest and this is very much more stable than the functional virus, the best harvesting time is evidently on or after the day of the highest virus titre. On the other hand, the high growth rate of the head is an inducement to start harvesting as early as possible, at any rate before the start of the rapid growth observed from the 19th day, so that less harmful head tissue has to be processed:

| Age of the embryo (days) | 17 | 18 | 19 | 20 | 21 | 22 | 23 |
|---|---|---|---|---|---|---|---|
| Weight of heads (per 20) in g | 62 | 60 | 76 | 88 | 100 | 131 | 135 |
|  |  | 65 | 67 | 89 | 112 | 115 |  |
|  |  |  | 83 | 91 | 99 |  |  |
| Individual head (g) | 3.1 | 3.1 | 3.8 | 4.5 | 5.2 | 6.2 | 6.8 |

3. Effectiveness of the Rabies Vaccine, obtained according to Example 1, in Cats after Subcutaneous Vaccination

| Number of vaccinated subjects with more than | Male Cats 7 | Female Cats 7 |
|---|---|---|
| 0.5 IU | 100% | 100% |
| 5.0 | 57 | 29 |
| 20.0 | 43 | 14 |
| (International Units of Antibody Content) |  |  |

4. Effectiveness in Monkeys (macacus rhesus

| Vaccine | According to Example 1 | | Commercial Vaccine "Merieux" (HDCS) | |
|---|---|---|---|---|
| Vaccination plan (days) | 0,3,7 | 0,3 | 0,3,7 | 0,3 |
| Number of monkeys | 5 | 5 | 5 | 5 |
| Antibodies (≧0.5 IU) 3 weeks after the last vaccination | 5 (100%) | 4 (80%) | 1 (20%) | 1 (20%) |
| 7 weeks after the last vaccination | 4 (80%) | 3 (60%) | 3 (60%) | 0 (0%) |

5. Effectiveness of the Rabies Vaccine, obtained according to the Invention, in Humans Vaccinations of humans were carried out over 70 times using the finished, lyophilized and thoroughly tested vaccine in comparison with a HDCS (human diploid cell strain) vaccine. The harmlessness of the new vaccine was at least as good as that of the standard vaccine.

| Vaccines | Vaccine according to Example 1 | Commercial Vaccine "Merieux" (HDCS) |
|---|---|---|
| Doses vaccinated | 74 | 70 |
| Local reaction (heat, swelling, reddening) | 2 (2.7%) | 8 (11.4%) |
| General reaction (fever, rash, confinement to bed) | - (0%) | 2 (2.8%) |

The effectiveness of the new vaccine was also compared with that of the standard vaccine. The following table shows the percentage of persons who reacted after vaccination with one or other of the vaccines by development of antibodies, 0.5 IU (international unit) generally being regarded as protective.

| Number of vaccinated subjects with more than | Vaccine according to Example 1 (36 vaccinated subjects) | HDCS Vaccine "Merieux" (33 vaccinated subjects) |
|---|---|---|
| 0.5 IU of antibodies | 100% | 100% |
| 5.0 | 89% | 85% |
| 10.0 | 64 | 58 |
| 15.0 | 56 | 39 |
| 20.0 | 47 | 39 |
| 30.0 | 39 | 24 |
| 40.0 | 25 | 12 |

EXAMPLE 3

Manufacture of Chicken Embryo Vaccine

Chicken eggs are incubated for seven days at 36° C.±1° C. at 60 to 75% humidity. On the seventh day of incubation rabies vaccine is directly inoculated into the yoke-bag of the developing embryos in the eggs. Incubation is continued. 10 days later the eggs are opened and the embryos extracted. The embryos are cut up, their heads, spinal marrow and trunks are separately processed, that is comminuted in each case to give a 10% homogenate. The virus concentration in the homogenate is titrated using a rapid fluorescent focus inhibition test (RFFIT).

Three series of tests were carried out and the results are shown in the table set out below.

| | Concentration of virus in ID 50/ml | |
|---|---|---|
| Head | 4.25/4.4 | & 4.8 |
| Spinal Marrow | 3.55 | & 4.8 |
| Trunk | 3.0 /3.6 | & 3.8 |

Definition of ID 50/ml = virus titre $\times$ log$_{10}$ = factor of the minimum concentration to infect 50% of tissue cultures.

It was discovered that the tissue of the central nervous system (CNS) contained about 10 times as much virus as the CNS-free rump.

Based on this result, production of chicken embryo vaccine was carried out in an exactly similar manner to that of Example 1 in that rabies virus adapted to chicken embryo cells and of high titration values is bred in partially incubated chicken eggs in accordance with, for example, the method of H. Koprowsky, Laboratory Techniques in Rabies by M. M. Kaplan et al, WHO Geneva, Chapter 26, pp. 235-242. The eggs are inoculated on the seventh day of incubation and following this, they are further incubated. Nine to ten days after inoculation of the virus into the yoke-bag, the chicken embryo heads are harvested. The chicken embryo heads are processed according to the method described in Example 1. The vaccine so produced is subjected to the quality controls described in Example 1.7. The vaccine also proved to be fully active in humans.

EXAMPLE 4

In a similar manner to that described in Example 1, rabies viruses can also be multiplied in quails' eggs which have started to hatch and then harvested from their heads.

What is claimed is:

1. In a method for the preparation of rabies vaccine wherein rabies viruses are multiplied in poultry embryos, the embryos are harvested and a cell extract containing the rabies antigen is separated therefrom and processed for use, the improvement which comprises harvesting only the heads of the embryos and separating the antigen by differential centrifugation and density gradient centrifugation.

2. The method of claim 1 wherein the embryos are duck embryos, chicken embryos, or quail embryos.

3. The method of claim 1 or 2 wherein the differential centrifugation is carried out at about 10,000 to 15,000 xg and the density gradient centrifugation is carried out at 75,000 to 90,000 xg in increasing sugar concentrations and in buffer solution.

* * * * *